Figure 1:
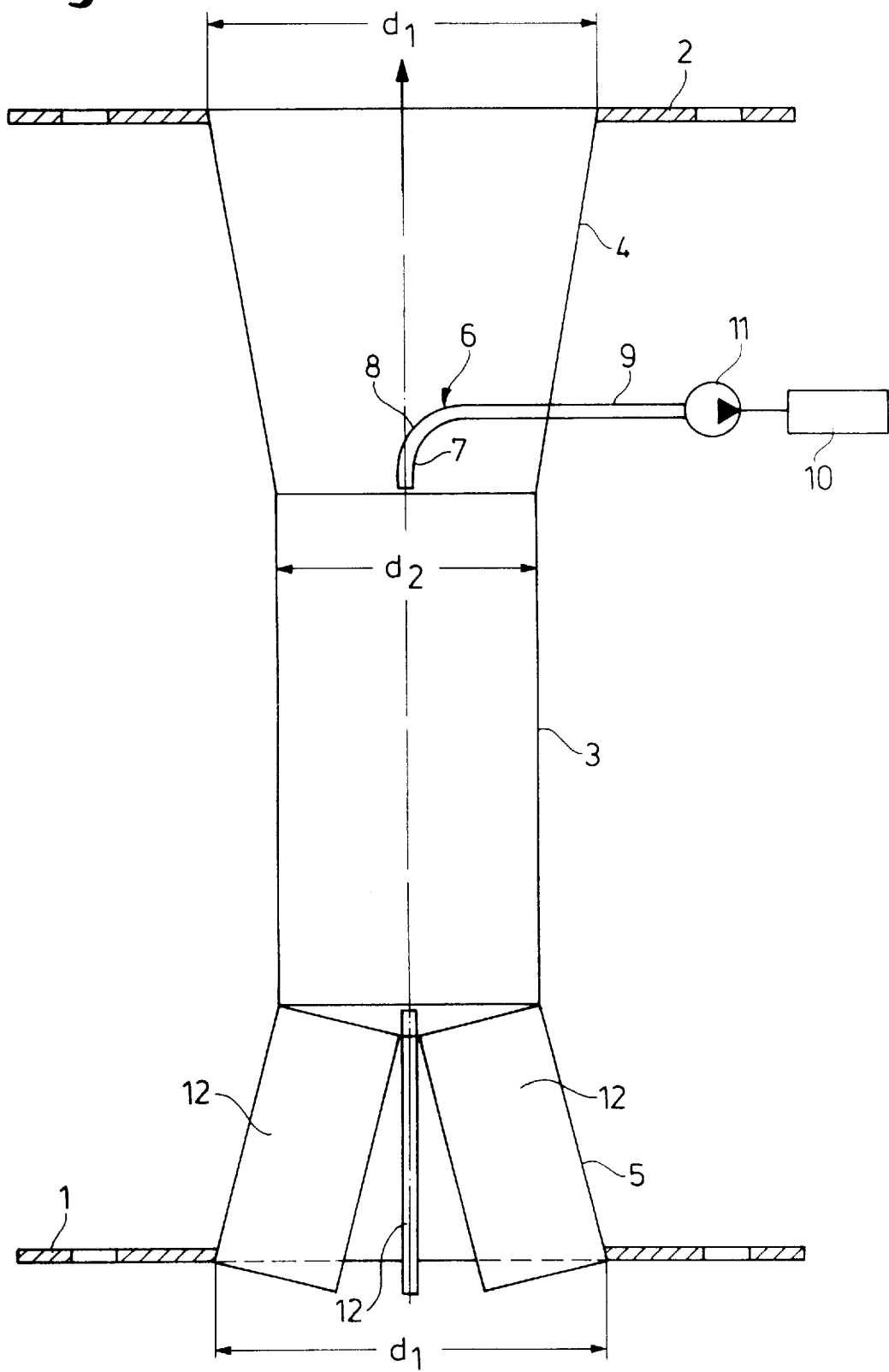

United States Patent

Ulfik et al.

[11] Patent Number: 5,841,037
[45] Date of Patent: Nov. 24, 1998

[54] PROCESS FOR SAMPLING IN PARTICLE-LADEN GAS STREAMS

[75] Inventors: Benno Ulfik, Leverkusen; Mathias Benz, Bergisch Gladbach; Jörg Rainer Schmitz, Schwerte; Heiko Herold, Neuss, all of Germany

[73] Assignee: Bayer Aktiengesellschaft, Leverkusen, Germany

[21] Appl. No.: 807,188

[22] Filed: Feb. 27, 1997

[30] Foreign Application Priority Data

Mar. 4, 1996 [DE] Germany .................. 196 08 242.0

[51] Int. Cl.$^6$ ...................................... G01N 1/00
[52] U.S. Cl. ........................................... 73/863
[58] Field of Search ................ 73/863, 863.43, 73/863.58, 23.33, 865.5

[56] References Cited

U.S. PATENT DOCUMENTS

| | | | |
|---|---|---|---|
| 3,827,297 | 8/1974 | Griverus | 73/861.32 |
| 4,060,001 | 11/1977 | Archerd | 73/863.58 |
| 4,361,028 | 11/1982 | Kamiya et al. | 73/23.33 |
| 4,602,743 | 7/1986 | Nied | 241/5 |
| 4,633,706 | 1/1987 | Ito et al. | 73/23.23 |
| 4,823,591 | 4/1989 | Lewis . | |
| 5,604,319 | 2/1997 | Kohsaka et al. | 73/863.43 |

FOREIGN PATENT DOCUMENTS

| | | |
|---|---|---|
| 0658756 | 6/1995 | European Pat. Off. . |
| 3837232 | 5/1989 | Germany . |
| 290246 | 5/1991 | Germany . |
| 4115212 | 11/1992 | Germany . |
| 2175414 | 11/1986 | United Kingdom . |

OTHER PUBLICATIONS

A. Bürkholz, Staub —Reinhaltung der Luft, 51, pp. 395 –400, (1991).
R. Nied, Aufbereitungs–Technik, 23, 5, p. 236, (1982).

Primary Examiner—Ronald L. Biegel
Assistant Examiner—Jewel V. Thompson
Attorney, Agent, or Firm—Sprung Kramer Schaefer & Briscoe

[57] ABSTRACT

In the process for the continuous collection of pulverulent or dusty samples from a particle-laden stream, a sample stream is drawn off from a particle-laden main stream in a pneumatic conveying line 17 and passed via a collection line 9 to a particle size measurement device 10. In order to reduce spin, the main stream in the conveying line 17 is passed through a venturi-like cross-sectional constriction 3, 4, 5, the cross-sectional area of which is 10 to 60% of the free cross-sectional area of the conveying line 17. Samples are then collected downstream from the cross-sectional constriction through one or more probe tubes 7, wherein a partial stream is collected from the main stream parallel to the direction of flow thereof. In conjunction with a jet mill 14, into which the product to be ground and the propellant air are continuously introduced, the particle size distribution measured in the continuously collected sample stream may be used as a control parameter in order to adjust a parameter which determines particle size distribution of the jet mill 14 in such a manner that the particle size distribution in the product stream remains constant.

6 Claims, 4 Drawing Sheets

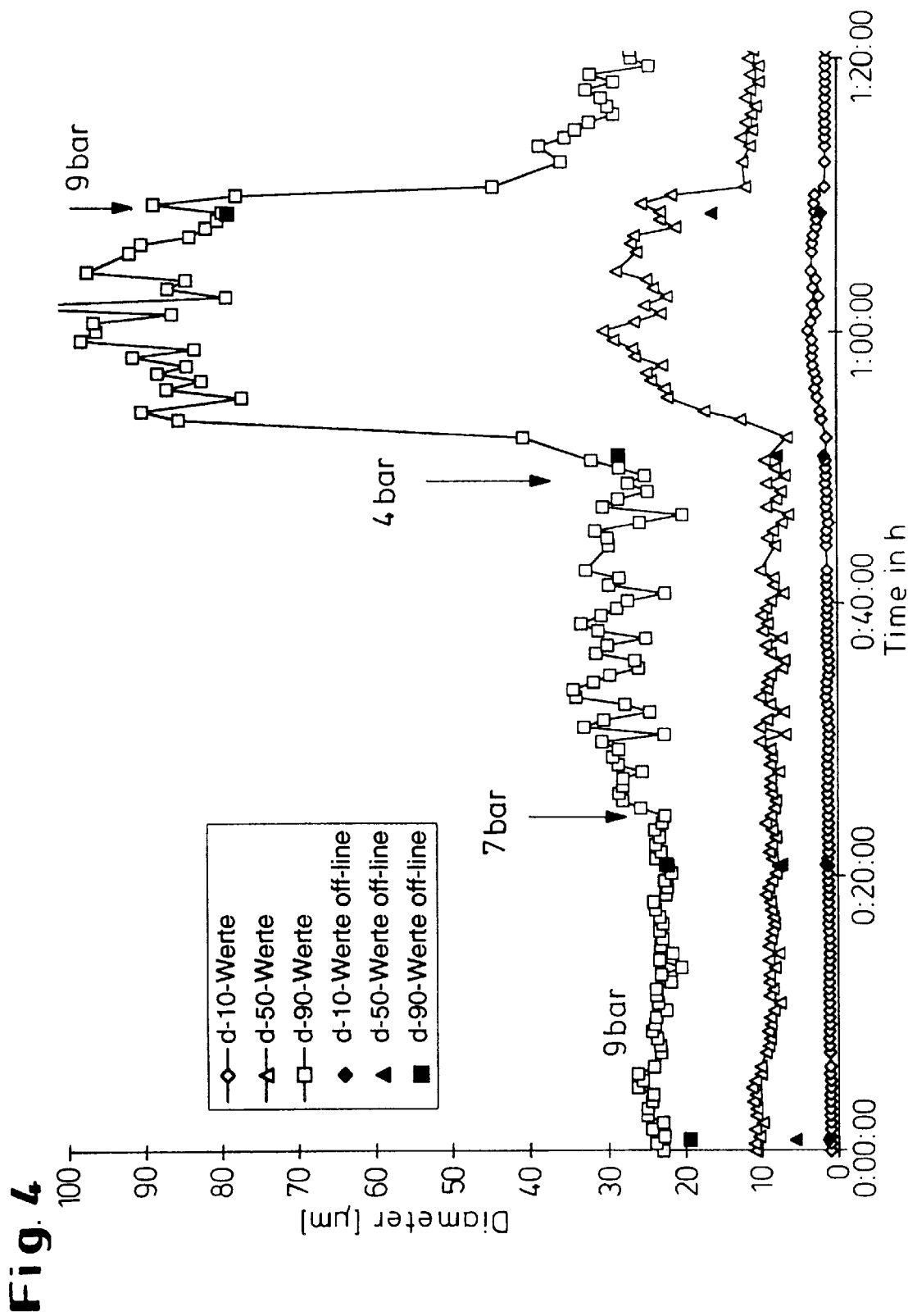

PROCESS FOR SAMPLING IN PARTICLE-LADEN GAS STREAMS

This invention relates to a process for the continuous collection of pulverulent samples from a particle-laden stream, in which a sample stream is drawn off from a particle-laden main stream in a pneumatic line and passed via a collection line to a measurement device.

Various commercial sampling probes are known for taking samples from pneumatic conveying lines. It has, however, been found that systematic measurement errors may occur, which are frequently dependent upon the position of the sampling probe in the conveying line. It is known from investigations by A. Burkholz, *Staub Reinhaltung der Luft*, 51 (1991), pages 395–400, that, when using collection probes for particle measurement, a representative sample of the particles transported in the conveying line air stream is obtained only if the sample is taken at an identical velocity while as far as possible avoiding any deviation in the flow lines of the air on entry into the probe. These criteria are described as isokinetic collection conditions.

An object of the present invention is to draw off a representative partial stream from the main stream in a product-laden, pneumatic conveying line while ensuring isokinetic collection conditions in order to subject this partial stream to continuous particle size analysis. In a further stage, particle size analysis is then to be used for automatically establishing and adjusting the particle size of a particle-laden product stream leaving a jet mill or a pneumatic classifier.

This object is achieved according to the invention by passing the main stream through a conveying line having a venturi-like cross-sectional constriction in order to reduce spin, the constriction having a cross-sectional area of 10% to 60% of the free cross-sectional area of the conveying line and, downstream from the cross-sectional constriction, using one or more probe tubes to collect a partial stream from the main stream parallel to the direction of flow thereof.

A further improvement in reducing spin may be achieved by rotationally symmetrical guide vanes located within the cross-sectional constriction and arranged paraxially or obliquely.

According to a preferred embodiment of the invention, the sample is collected from the main stream through two or more probe tubes, which are combined into a common collection line.

In the course of further development, the sampling according to the invention is used in conjunction with particle size control. In this manner, particle, size may be held constant in a product-laden air stream. This process is particularly suitable in jet mills, for example in a spiral jet mill or fluidised bed opposed-jet mill, in which the product to be ground and propellant gas are continuously introduced and a main product stream is continuously discharged from the outlet. The particle size distribution of the sample stream collected from the product stream is here advantageously also continuously measured and the product feed stream or the propellant gas mass flow or grinding jet admission pressure and, in the case of a fluidised bed opposed-jet mill, preferably the rotational speed of an integral blade wheel classifier, are adjusted in such a manner that a preset particle size distribution value is maintained in the product stream.

The following advantages are achieved with the invention:

The process according to the invention establishes the functional preconditions for representative and uniform sampling in pneumatic conveying lines under isokinetic conditions with the associated increased measurement accuracy. Furthermore, the probe is of a simple and robust design and may be used in many applications. In conjunction with jet mills, including the collection probe in a measurement and control system allows a desired set value for particle size distribution to be established and maintained.

Figure 2:
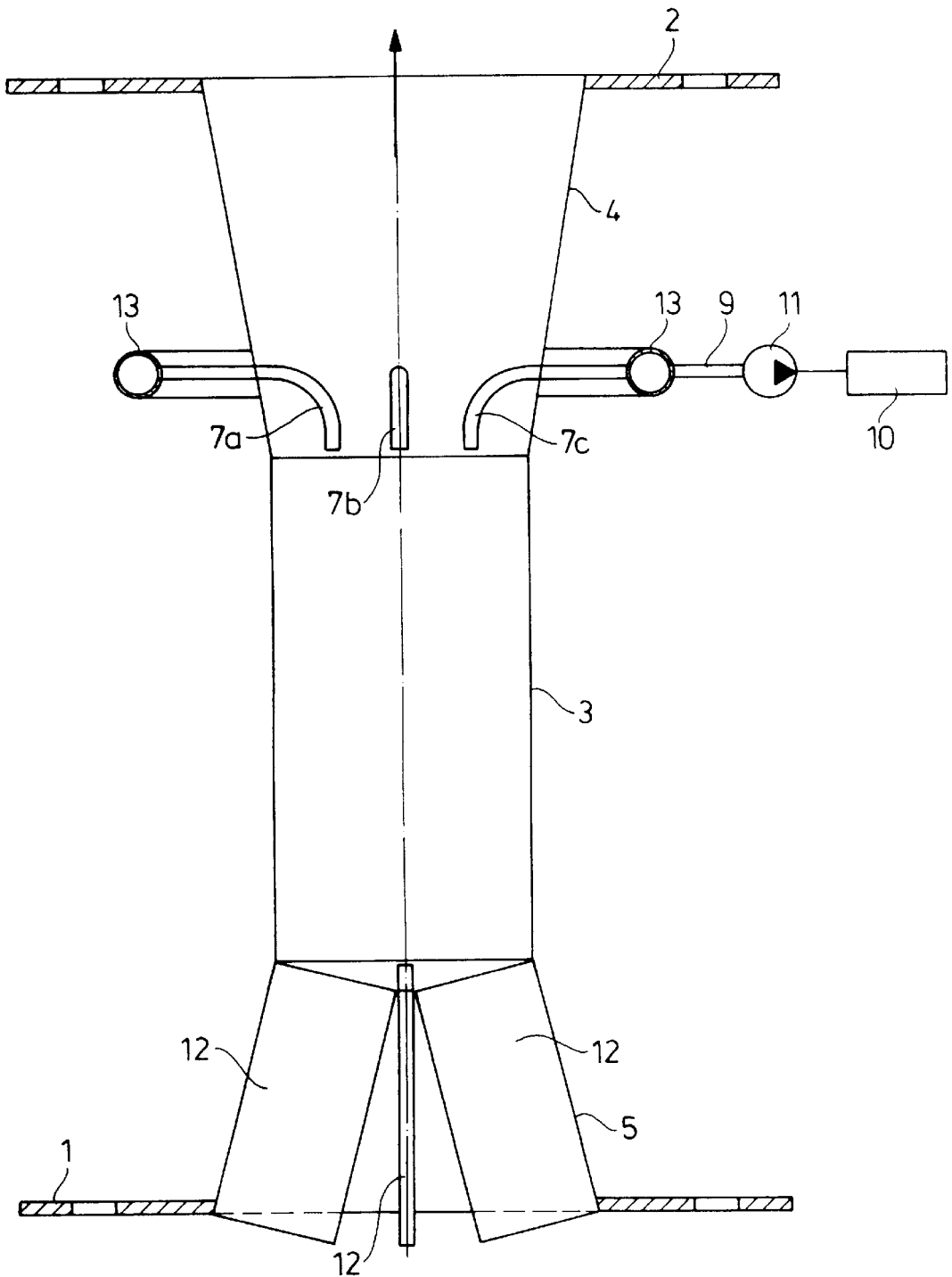
Figure 3:
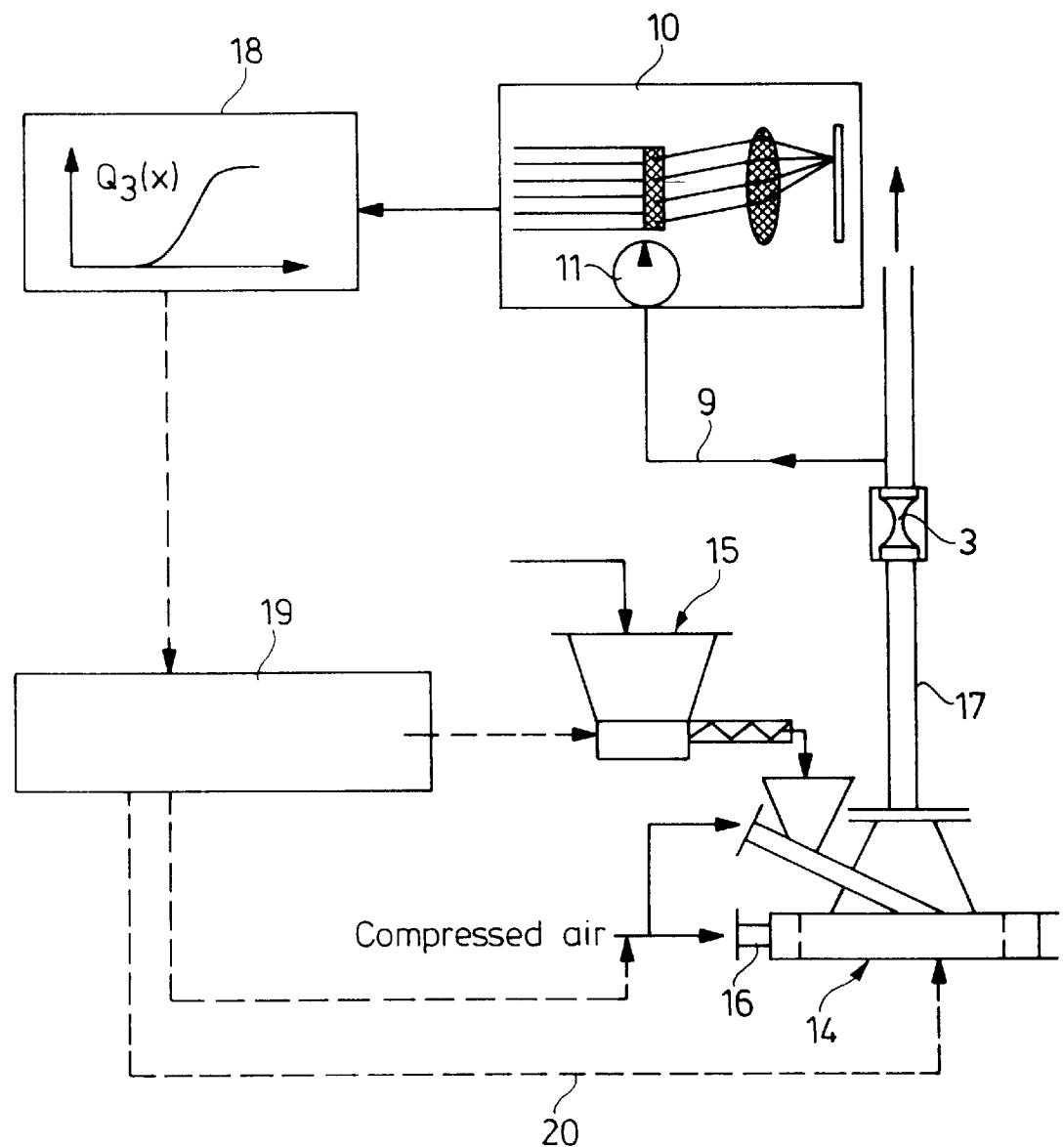

The following drawings and practical examples illustrate the invention in greater detail. The drawings show:

FIG. 1 a section from a conveying line for a main product stream with a cross-sectional constriction and a collection tube for the sample, FIG. 2 a conveying line similar to FIG. 1 with two or more collection tubes which combine into an annular line, FIG. 3 a flow chart for on-line control of particle size in a grinding unit using the isokinetic collection probe according to FIG. 1 or FIG. 2 and FIG. 4 a measurement example for continuous on-line acquisition of the particle size distribution of ground sugar (test product) in the main stream of a spiral jet mill at various grinding jet admission pressures.

A particle-laden air stream (main stream) passes through the section of a conveying line shown in FIG. 1 in the direction of the arrow. The section consists of flanges 1 and 2 for installation in the conveying line, a tube section with a narrowed cross-section 3, a conical tube section 4 widening in the direction of flow and a converging conical tube section 5 at the entry to the cross-sectional constriction 3. The taper of tube section 4 is, for example 10°, and that of tube section 5 is for example 14°. The ratio $d_1:d_2$ of the diameters of the conveying line and the cross-sectional constriction 3 is in the range from 0.3 to 0.8. A collection probe 6 in the form of an open axial probe tube 7 is located downstream from the cross-sectional constriction 3, which probe tube is connected via an elbow 8 with a collection line 9 arranged perpendicularly to the conveying line. This shape makes a substantial contribution to minimizing disruption to flow in the conveying line. The main stream impinges substantially perpendicularly onto the face of the opening of the axial probe tube 7 of the collection probe. A sample of the main stream is taken through the collection probe and passed via the collection line 9 to a particle size measurement device 10. To this end, an air jet injector 11, is fitted at the inlet to the measurement device 10, the suction power of which is calculated such that the flow velocity of the collected partial stream on entry into the axial probe tube 7 approximately matches that of the main stream. The cross-sectional constriction 3 renders flow at the collection point more uniform and smoother, i.e. on entry into the probe tube 7.

The smoothness and uniformity of flow may be further improved by rotationally symmetrical guide vanes 12 located within the conical tube section 5. According to FIG. 1 and FIG. 2, four guide vanes 12 are uniformly arranged circumferentially. Such guide fins may in particular effectively smooth flow which has a spin component, which is frequently observed in the product streams (product discharge) from jet mills. The guide fins 12 may also be arranged obliquely relative to the direction of flow. In this case, care must be taken to select the angle of attack such that any spin component present in the main stream is not amplified, but instead diminished. Ensuring that flow is smooth and uniform is an essential precondition for reproducible and representative sampling from the particle, laden main stream under isokinetic conditions. If this is not achieved, considerable deviations with regard to particle size distributions in the main stream and collected partial stream could occur, such that sampling would not be representative of the main stream and a systematic error would be introduced into the measurement.

According to an alternative embodiment, as shown in FIG. 2, two or more (three) probe tubes 7a, 7b, 7c are arranged in a plane downstream from the cross-sectional constriction 3 at the junction with the conically diverging tube section 4. The three probe tubes 7a, 7b, 7c combine into an annular line 13 enclosing the conveying line and are connected to the collection line 9. This arrangement has the advantage that local irregularities in particle distribution in the main stream are averaged out.

FIG. 3 is a schematic diagram of a control circuit including the sampling described above for establishing and maintaining particle size in a conveying line 17 connected with the outlet from a spiral jet mill 14. The spiral jet mill is a particular type of air jet mill. The product to be ground is introduced into the spiral jet mill 14 by means of a metering device 15. The spiral jet mill is additionally supplied with compressed air via the port 16. The ground product is discharged through the conveying line 17, in which the cross-sectional constriction 3 described above is located. As described above, downstream from the cross-sectional constriction 3, a partial stream is branched off through collection line 9 from the particle-laden air stream (main stream) flowing through the conveying line 17 and introduced into the particle size measurement device 10, which operates by laser light diffraction. The mass flow of the partial stream is approximately 1% to 3% of the mass flow of the main stream. A suitable particle measurement device is, for example, the HELOS device from Sympatec (Clausthal Deutschland). This device provides direct (on-line) characteristic values for the particle size distribution of the collected sample, for example the $d_{10}$, $d_{50}$ or $d_{90}$ value. The $d_{10}$ value is, for example, defined as the diameter at which 10% of the particles have a diameter smaller than $d_{10}$, and 90% of the particles have a diameter larger than $d_{10}$. The $d_{50}$ value corresponds to the mean particle diameter. The output signal from the particle measurement device 10 is sent to a measurement computer 18, in which the measurement signal is compared with a preset value for particle size. A derived measurement, such as for example the specific surface area of the particles, may be calculated using the measurement computer and used as a control parameter.

The measurement computer 18 output is connected with a control unit 19, which produces a control signal to adjust the compressed air stream at port 16 of the spiral mill 14. Another option is to alter the product feed stream by means of the metering device 15. Adjustment is made, as is conventional in all controllers, in such a manner that the preset value for particle size distribution in the main stream of the conveying line 17 remains constant. The stated control circuit is also suitable for other mills operated with air or inert gas, in particular for fluidized bed opposed-jet mills. The design and mode of action of this type of mill are known from the literature (see, for example, Dr. R. Nied, *Aufbereitungs-Technik*, 23 (1982) 5, page 236 and DE 3 338 138), so it is possible to dispense with a more detailed description at this point. Since this type of mill usually has an integral (built in) blade wheel classifier to classify the particles, one possible option is to use the rotational speed of the blade wheel classifier as a control parameter to control particle size distribution, i.e. in this case the control unit 18 must provide a control signal (via line 20) to alter the rotational speed of the blade wheel classifier.

MEASUREMENT EXAMPLE

The particle measurements (particle size distribution as a function (if time) shown in the diagram in FIG. 4 were made on a spiral jet mill according to FIG. 3. The test product used was granulated sugar, which was ground to icing sugar in the spiral jet mill 14. Mass flow in the conveying line 17 was 90 kg/h, that of the derived sample stream downstream from the cross-sectional constriction 3 was 0.9 to 1.8 kg/h. The grinding jet admission pressure at port 16 of the spiral jet mill was additionally varied at given intervals in time as an operating parameter (pressure values 9 bar→7 bar→4 bar→9 bar). The plotted values are the $d_{10}$, $d_{50}$ and $d_{90}$ values measured with the laser diffractometer 10. By way of control, the icing sugar from the main stream in the conveying line 17 was separated at various points in time with a cyclone separator and the particle size distribution (again the $d_{10}$, $d_{50}$ and $d_{90}$ values) of these specimens was determined statically, i.e. off-line with a second laser diffractometer. The good match between the dynamic (on-line) and static (off-line) measurements may be seen.

We claim:

1. Process for the continuous collection of pulverulent samples from a particle-laden stream, in which a sample stream is drawn off from a particle-laden main stream in a pneumatic conveying line (17) and passed via a collection line (9) to a particle size measurement device (10), wherein the main stream is passed through a conveying line (17) having a venturi-like cross-sectional constriction (3, 4, 5) in order to reduce spin, the cross-sectional area of which is 10 to 60% of the free cross-sectional area of the conveying line (17) and that, downstream from the cross-sectional constriction (3, 4, 5), a partial stream is collected through one or more probe tubes (7) from the main stream parallel to the direction of flow thereof.

2. Process according to claim 1, wherein the spin is additionally reduced by rotationally symmetrical guide vanes (12) located within the cross-sectional constriction (3, 4, 5) and arranged paraxially or obliquely.

3. Process according to claim 1, wherein the collection is made through two or more probe tubes (7a, 7b, 7c), which are combined into a common collection line (9).

4. Process according to claim 1, wherein the partial stream is collected from the main product stream at the outlet from an air jet mill (14), into which the product to be ground and propellant air are continuously introduced, that the particle size distribution of the sample stream is measured and the product feed stream and/or the mass flow of propellant air in the air jet mill (14) are adjusted in such a manner that the particle size distribution in the product stream remains constant.

5. Process according to claim 4, wherein the partial stream is collected from the main product stream at the outlet of a blade wheel classifier, into which the product to be classified from the air jet mill outlet and the classifying air are continuously introduced, that the particle size distribution of the sample stream is measured and the product feed stream in the air mill and/or the mass flow of classifying air and/or the rotational speed of the blade wheel classifier are adjusted in such a manner that the mean particle size in the product stream remains constant.

6. Process according to claim 1, wherein the partial stream is collected from the main product stream at the outlet from a fluidized bed opposed-jet mill, into which the product to be ground and conveying air are continuously introduced, that the particle size distribution of the sample stream is measured and the product feed stream and/or the grinding jet admission pressure and/or the rotational speed of a blade wheel classifier integrated in the fluidized bed opposed-jet mill are adjusted in such a manner that the particle size distribution in the product stream remains constant.

* * * * *